(12) United States Patent
Gamble et al.

(10) Patent No.: US 7,141,611 B2
(45) Date of Patent: *Nov. 28, 2006

(54) HIGH MOLECULAR WEIGHT PRIMARY ALIPHATIC ALCOHOLS OBTAINED FROM NATURAL PRODUCTS AND USES THEREOF

(75) Inventors: William R. Gamble, Longmont, CO (US); Zhengjie Liu, Superior, CO (US); David T. Bailey, Boulder, CO (US); Pedro P. Perez, Hialeah, FL (US); Dean P. Stull, Longmont, CO (US); Steven L. Richheimer, Westminster, CO (US); Rebecca L. Nichols, Broomfield, CO (US); Rod Lenoble, Westminster, CO (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/622,249

(22) Filed: Jul. 18, 2003

(65) Prior Publication Data

US 2004/0019119 A1 Jan. 29, 2004

Related U.S. Application Data

(63) Continuation of application No. 10/133,986, filed on Apr. 25, 2002, now Pat. No. 6,596,776, which is a continuation-in-part of application No. 09/949,285, filed on Sep. 7, 2001, now abandoned, which is a continuation-in-part of application No. 09/845,043, filed on Apr. 27, 2001, now abandoned, which is a continuation-in-part of application No. 09/337,339, filed on Jun. 21, 1999, now Pat. No. 6,225,354.

(60) Provisional application No. 60/236,515, filed on Sep. 29, 2000.

(51) Int. Cl.
*A61K 31/045* (2006.01)
*C07C 29/76* (2006.01)
*C07C 29/28* (2006.01)
*C07C 29/86* (2006.01)

(52) U.S. Cl. .............. 514/724; 514/164; 568/840; 568/913; 568/918

(58) Field of Classification Search ............... 514/164, 514/724; 568/840, 913, 918
See application file for complete search history.

(56) References Cited

U.S. PATENT DOCUMENTS

| | | | | |
|---|---|---|---|---|
| 5,663,156 | A * | 9/1997 | Granja et al. | 514/164 |
| 6,235,795 | B1 * | 5/2001 | Hernandez et al. | 514/724 |
| 6,423,697 | B1 * | 7/2002 | Friedman | 514/164 |
| 6,596,776 | B1 * | 7/2003 | Gamble et al. | 514/724 |

* cited by examiner

*Primary Examiner*—Peter O'Sullivan
(74) *Attorney, Agent, or Firm*—Hogan & Hartson, LLP (57) ABSTRACT

This invention provides an isolated mixture of higher molecular weight primary aliphatic alcohols having 20, 22, 24, 26, 27, 28, 30, 32 and 34 carbon atoms and having enhanced purity. This invention also provides a process for obtaining the alcohol mixture by extracting a natural product with organic solvents with or without saponification of the natural product. The alcohol mixture is useful in pharmaceutical compositions, foodstuffs and dietary supplements and is effective for lowering total cholesterol and LDL-cholesterol and increasing HDL-cholesterol levels and therefore is effective in treating hypercholesterolemia. The composition may be used to reduce the risk of coronary heart disease, to inhibit the atherosclerotic process (platelet hyperaggregability, ischemia and thrombosis), and can be used as an anti-inflammatory and anti-thrombotic agent. The composition also possesses neurotrophic properties and is useful for improving male sexual activity.

5 Claims, 6 Drawing Sheets

Figure 1

Saponification increases the theoretical yield of the aliphatic alcohols

Before saponification - ~1 -6% aliphatic alcohols
After saponification - ~25 -30% aliphatic alcohols

- Dissolve solids in acetone and reflux
- Hot Filtration
- Purity > 80% aliphatic alcohols
- Recovery ~ 45%

Figure 6

HIGH MOLECULAR WEIGHT PRIMARY ALIPHATIC ALCOHOLS OBTAINED FROM NATURAL PRODUCTS AND USES THEREOF

CROSS-REFERENCE TO OTHER APPLICATIONS

This patent application is a continuation of U.S. patent application Ser. No. 10/133,986, filed Apr. 25, 2002, now U.S. Pat. No. 6,596,776, which is a continuation-in-part of U.S. Pat. No. 09/949,285, filed Sep. 7, 2001, now abandoned, which is a continuation-in-part of U.S. patent application Ser. No. 09/845,043, filed Apr. 27, 2001, now abandoned, which is a continuation-in-part of U.S. patent application Ser. No. 09/337,339, now issued U.S. Pat. No. 6,225,354, filed Jun. 21, 1999. U.S. patent application Ser. No. 10/133,986 also claims benefit of Provisional Application No. 60/236,515 filed on Sep. 29, 2000. All of the above-referenced applications are incorporated herein by reference.

BACKGROUND OF THE INVENTION

1. Field of the Invention

The present invention pertains to a biologically active mixture of high purity, high molecular weight straight chained primary aliphatic alcohols (referred to herein as aliphatic alcohols) having enhanced purity that is isolated from a naturally occurring source. More particularly the invention pertains to a mixture of high purity, high molecular weight straight chained primary aliphatic alcohols that is obtained from saponified and/or unsaponified starting materials by liquid extraction, wherein the resulting aliphatic alcohols in the mixture contain 20 to 34 carbon atoms.

2. Description of the State of Art

All kinds of waxes, and more especially beeswax, have always been a matter of interest. This has been the case not only because of their industrial applications, but also because of their chemical composition. The amount of beeswax in honey ranges between 0.9% to 1.13%, depending on the methods used to separate the wax from the honey. This wax contains esters, hydrocarbons, free fatty acids, free alcohols and a long list of minor compounds.

The natural mixture of aliphatic alcohols obtained from beeswax has been studied by several authors to learn about its composition and main features. The obtaining of different mixtures of aliphatic alcohols from various waxes has also been reported. (J. A. Lamberton, et al., *Australian Journal of Chemistry*, 13:261–268 (1959); A. Horn and J. S. Martic, *Journal of Science Food and Agriculture*, 10:571 (1957); Kreger, (1948); Wimbero, (1904); and Mitsui and Col, (1942)). These studies suggest a method for obtaining aliphatic alcohols based on the homogeneous saponification with alcoholic potassium hydroxide.

Another method reports an extraction of the natural aliphatic alcohol mixture through a high efficiency vacuum. The high vacuum wax distillation for the chemical isolation of mixed derivatives and the extraction of the remaining wax are done using petroleum ether. The solvent is evaporated and the remaining solids are acetylated for further purification through alumina chromatography. Finally, through alkaline hydrolysis, aliphatic alcohols are obtained and then recrystallized in ethanol, showing a melting point range from 62° C. to 82° C.

Blood-lipid lowering effects of a natural mixture of straight chain aliphatic alcohols have been demonstrated by several authors: (F. Liu, et al., "Active Constituents Lowering Blood-Lipid in Beeswax," *Zhongguo Zhong Yao Zhi*, 21(9):553–4, 576 (1996)); (H. Sho, et al., "Effects of Okinawa Sugar Cane Wax and Fatty Alcohols on Serum and Liver Lipids in the Rats," *J Nutri Vitaminol*, 30(6):553–559 (1984)); (S. Kato, K. Hamatani, et al., "Octacosanol Effects Lipid Metabolism in Rat Fed on a High Fat Diet," *Br J Nutr*, 73(3):433–441 (1995)); and (Kabiry, et al., "Tissue Distribution of Octacosanol in Liver and Muscle of Rats After Serial Administration," *Ann Nutr Metab*, 39(5):279–284 (1995)); and (I. Gouni-Berthold, et al., "Policosanol: Clinical pharmacology and therapeutic significance of a new lipid-lowering agent," *Am Heart J*, 143:356–365 (2002)). Many investigational studies based on clinical studies using the natural mixtures of straight chain aliphatic alcohols have been published.

A procedure for obtaining a natural mixture of aliphatic alcohols from animal and vegetable waxes (a natural sourced wax) is also known in the prior art. This prior art procedure is based on the extraction of alcohol mixtures with fluid extractant in the sub- and super-critical states between 20° C. and 100° C. Selective extraction can be carried out with this procedure, but when this is applied to beeswax it is only possible to obtain between 10% to 15% of a C-20 to C-34 alcohol mixture.

Another project (S. Inaa, K. Furukama, T. Masui, K. Honda, J. Ogasawara, and G. Tsubikamoto, "Process for Recovering Primary Normal Aliphatic Higher Alcohols" JP 60-119514 (1996)) proposed a very similar extraction method applied to waxes that is based on fluids ($CO_2$ with ethylene) in sub- and super-critical states.

There are several different commercial dietary supplements, foods and drugs that aid in the lowering of total blood cholesterol (lowering lipid, LDL-cholesterol, and total cholesterol levels) which are considered as effective, safe and well-tolerated but most produce different adverse side effects. Since lipid-lowering therapy must be chronically administered, safety and tolerability are very important for their definitive acceptance.

It has been described that treatment with some lipid-lowering drugs reduces the tendency for platelet hyperaggregation frequently seen in hyperlipidemic patients and experimental data have shown anti-aggregatory effects mediated by these compounds. Nevertheless, only some cholesterol-lowering drugs show this property.

Atherosclerosis is a variable combination of changes of the intima of the arteries consisting of the focal accumulation of lipids, complex carbohydrates, blood and blood products, fibrous tissue and calcium deposits, frequently also associated with medial changes. Thus, atherosclerosis is known as a multifactorial process and includes hyperlipidemia as a risk factor.

Among the factors contributing to atherosclerosis development, platelet aggregation has a very important place. The granule contents released from platelets activate arachidonic acid, which metabolizes into cyclic endoperoxides. These are mainly transformed into thromboxane $A_2$ ($TXA_2$), a strong vasoconstrictor and platelet aggregatory agent. Platelet aggregation can be elicited by numerous compounds, such as collagen, ADP, and epinephrine. Thus, different experimental "in vivo," "ex vivo," or "in vitro" models that test effectiveness of putative antiplatelet drugs commonly test their effect on platelet aggregation induced by these agents. These tests are also used for testing platelet aggregation in healthy volunteers and in patients with diseases which induce hyperaggregability such as hypercholesterolemia and diabetes.

Collagen-induced platelet aggregation is one of the most frequently used tests. Thus, for example, collagen injected intravenously leads to reversible intravascular platelet aggregation "in vivo" and aggregates of platelets enter the vascular microcirculation, subsequently decreasing the count of circulating platelets and simultaneously increasing the plasma malondialdehyde (MDA) concentration. Moreover, in some species the injection of collagen induces mortality produced by thrombosis. In these models, antiplatelet drugs generally prevent the decrease in circulating platelet content and the increase of MDA concentration, as well as collagen induced mortality.

Some drugs showing platelet anti-aggregatory effects are useful for treatment of thrombotic diseases, myocardial infarction, and stroke, but not all show these advantages. On the other hand, there are antithrombotic drugs such as streptokinase and urokinase that mainly act by lytic processes affecting blood coagulation, but not on the platelet aggregation. Since ischemic cardiovascular diseases, stroke and vascular peripheric obstructive pathologies are the main sequence of atherosclerosis, effects of several drugs on these complications are commonly tested. Thus, theoretically a drug showing cholesterol lowering properties that also can prevent these complications by acting on other events involved in these processes must be advantageous for treating these patients. Likewise, reduction of $TXA_2$ levels has been associated not only with antiplatelet and antithrombotic effects, but also with antischemic effects. The pharmacological screening of antischemic drugs commonly includes the evaluation of their effects on brain-induced global ischemia. Thus, the protective effect of different drugs on rat cerebral ischemia has been determined by this type of evaluation for certain non-steroidal anti-inflammatory drugs (NSAID) which inhibit reactions catalyzed by cyclooxygenase, as well as for specific inhibitors of thromboxane synthetase and prostacyclin ($PGI_2$) analogues (M. G. Borzeix and J. Cahn, "Effects of New Chemically Metabolically Stable Prostacyclin Analogues on Early Consequences of a Transient Cerebral Oligemia in Rats," *Prostaglandins*, 35(5):653–664 (1998)). Other experimental models, such as global ischemia induced experimentally in Mongolian gerbils, are also used frequently.

SUMMARY OF THE INVENTION

The method and resulting composition of the present invention comprises subjecting a natural product containing aliphatic alcohols present as esters to a homogenous phase saponification step, after which the saponified product is recovered, dried, and ground to a particle mesh size of 100–500 microns. Alternatively, the saponification step may be skipped entirely and the unsaponified natural product may be dried and ground to a particle mesh size of 100–200 microns.

Next, the particles of natural product containing the aliphatic alcohols (saponified or unsaponified) are placed into a conventional solid-liquid extractor, and a solvent is introduced and heated in contact with the natural product particles. The resulting solution is hot-filtered to remove the solids. The extract is then cooled to the temperature range of 2° C.–10° C. causing the aliphatic alcohols to solidify and form a suspension. The suspension is filtered, and the solids (first solids) are recovered and air dried. The solids obtained from this step are sent to a purifier where they are contacted with and dissolved in a second hot organic solvent. This solution is then hot-filtered and cooled. The solids (second solids) which form on cooling are again collected and dried by vacuum. The second solids are contacted with another hot organic solvent which dissolves the solids. This solution is hot-filtered and then chilled to resolidify the solids. These third solids are collected, dried and powdered and are the final product.

The final product contains a mixture of aliphatic alcohols from 20 to 34 carbon atoms comprising 1-eicosanol, 1-docosanol, 1-tetracosanol, 1-hexacosanol, 1-heptacosanol, 1-octacosanol, 1-triacontanol, 1-dotriacontanol and 1-tetratriacontanol having the following quantitative composition:

| 1-eicosanol | C-20 | 0–5% |
| --- | --- | --- |
| 1-docosanol | C-22 | 0–5% |
| 1-tetracosanol | C-24 | 12–30% |
| 1-hexacosanol | C-26 | 13–30% |
| 1-heptacosanol | C-27 | 0–5% |
| 1-octacosanol | C-28 | 12–25% |
| 1-triacontanol | C-30 | 20–40% |
| 1-dotriacontanol | C-32 | 5–15% |
| 1-tetratriacontanol | C-34 | 0–5% |

These solids may be used as is or reformulated for administration to humans and animals to reduce and/or prevent hypercholesterolemic diseases, total cholesterol, LDL-cholesterol, coronary heart disease (heart attacks and strokes), inflammation or immunoregulatory diseases, cardiovascular diseases, and/or neurodegenerative disorders. The daily dosage is established between 1 to 100 mg of aliphatic alcohol per day (preferably 3 to 20 mg) and is intended for ingestion in any type or form of foodstuff, capsule, tablet or liquid form.

BRIEF DESCRIPTION OF THE FIGURES

The accompanying drawings, which are incorporated in and form a part of the specification, illustrate the preferred embodiment of the present invention, and together with the description serve to explain the principles of the invention.

In the Drawings.

DETAILED DESCRIPTION OF THE INVENTION

The composition of the present invention is a mixture of high purity, high molecular weight straight chained primary aliphatic alcohols (herein referred to as aliphatic alcohols) obtained by saponifying (optional), extracting and purifying from starting materials, such as but not limited to, natural waxes, such as but not limited to, beeswax, carnauba wax, and candellia wax, bee pollen, oils, such as but not limited to, peanut oil, sesame oil, cod liver oil, rice bran oil, oat oil, and rosemary needles oil; and powders, such as but not limited to rice bran, containing primarily natural esters of aliphatic alcohols with carboxylic acids. For purposes of the remainder of this discussion beeswax is used to typify the starting material, however, it is to be understood that the process of the disclosed invention and the compositions derived therefrom may be achieved by utilizing the above-referenced starting materials.

The process of the present invention comprises subjecting the beeswax to a homogenous phase saponification step after which the saponified beeswax is dried and ground to a particle mesh size of 100–500 microns. Alternatively, unsaponified beeswax, of varying purity, may be used as the starting material and is initially dried and ground to a particle mesh size of 100–200 microns. The particles of saponified or unsaponified beeswax are placed into a conventional solid-liquid extractor and a hot organic solvent is introduced and contacted with the beeswax particles. The suspension is mixed and then hot-filtered to remove any solids.

The resulting extract is then maintained within the temperature range of 2° C.–10° C. causing the aliphatic alcohols to solidify and form a suspension. The suspension is filtered and the first solids are recovered and air dried. The dried solids obtained after drying are then sent to a purifier where they are contacted with and dissolved in a second hot solvent and hot-filtered. This solution is then cooled and the second solids collected and dried by vacuum. The dried solids obtained from the second purification step are contacted with another hot organic solvent, which dissolves the solids. This solution is hot-filtered and chilled, and the third solids collected, dried, and powdered to become the final product.

The final product, whether derived from saponified or unsaponified beeswax contains a mixture of aliphatic alcohols from 20 to 34 carbon atoms comprising 1-cicosanol, 1-docosanol, 1-tetracosanol, 1-hexacosanol, 1-heptacosanol, 1-octacosanol, 1-triacontanol, 1- dotriacontanol, and 1-tetratriacontanol having the following quantitative composition:

| 1-eicosanol | C-20 | 0–5% |
|---|---|---|
| 1-docosanol | C-22 | 0–5% |
| 1-tetracosanol | C-24 | 12–30% |
| 1-hexacosanol | C-26 | 13–30% |
| 1-heptacosanol | C-27 | 0–5% |
| 1-octacosanol | C-28 | 12–25% |
| 1-triacontanol | C-30 | 20–40% |
| 1-dotriacontanol | C-32 | 5–15% |
| 1-tetratriacontanol | C-34 | 0–5% |

This product has been developed for use in lowering LDL-cholesterol and total cholesterol, increasing HDL-cholesterol and improving the LDL-cholesterol/HDL-cholesterol ratio.

It has been discovered that the use of beeswax as the source of the aliphatic alcohol mixture offers numerous benefits which cannot be obtained when sugar cane wax is used as the source. For example, many factors are associated with purity levels of sugar cane wax which are difficult to control, and therefore it is difficult to obtain a reliable source of sugar cane wax which meets the requirements for consistently obtaining a uniform pure product.

In particular the purity level of sugar cane wax is influenced by the sugar cane variety, the age of the plant, the soil and climate conditions where the sugar cane is grown and the level and the type of fertilizer used to grow the sugar cane. In addition, the type of operational procedure used to extract the wax from the husk can influence the level of purity. None of these factors are significant when beeswax is used as the source for the alcohol mixture. Furthermore, minor variations in beeswax characteristics can be corrected by blending selected waxes which meet certain criteria with respect to parameters as further described herein.

Furthermore, preferred levels of certain operational parameters in the saponification (optional), extraction and purification processes have been discovered which lead to further enhancement of the purity level of the isolated aliphatic alcohols and enhanced percent recovery of the alcohols from the beeswax. These operational parameters include the following: particle size of the solid (i.e., the particle size of the saponified beeswax), alkali concentration, relationship between solid and liquid (i.e., solid:liquid ratio), temperature range, fluid regimen, crystallization regimen, hot-filtration regimen, centrifuge regimen and contact time. The preferred levels of these parameters (disclosed in U.S. Pat. No. 6,225,354) were established under experimental design in the laboratory as well as at the pilot plant and industrial levels.

Figure 1:
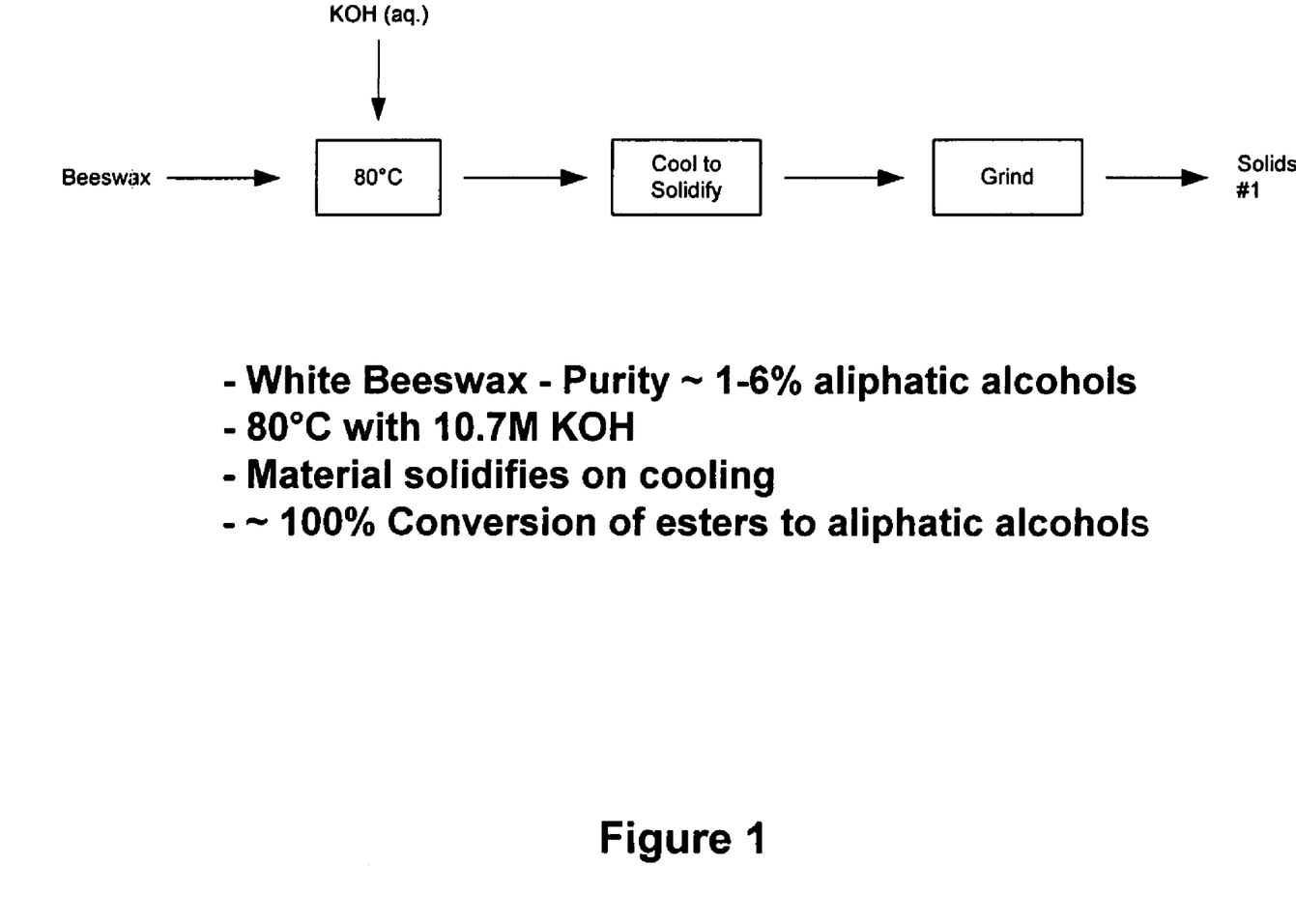
FIG. 1 is a flow diagram depicting the saponification step of the process according to the present invention.
Figure 2:
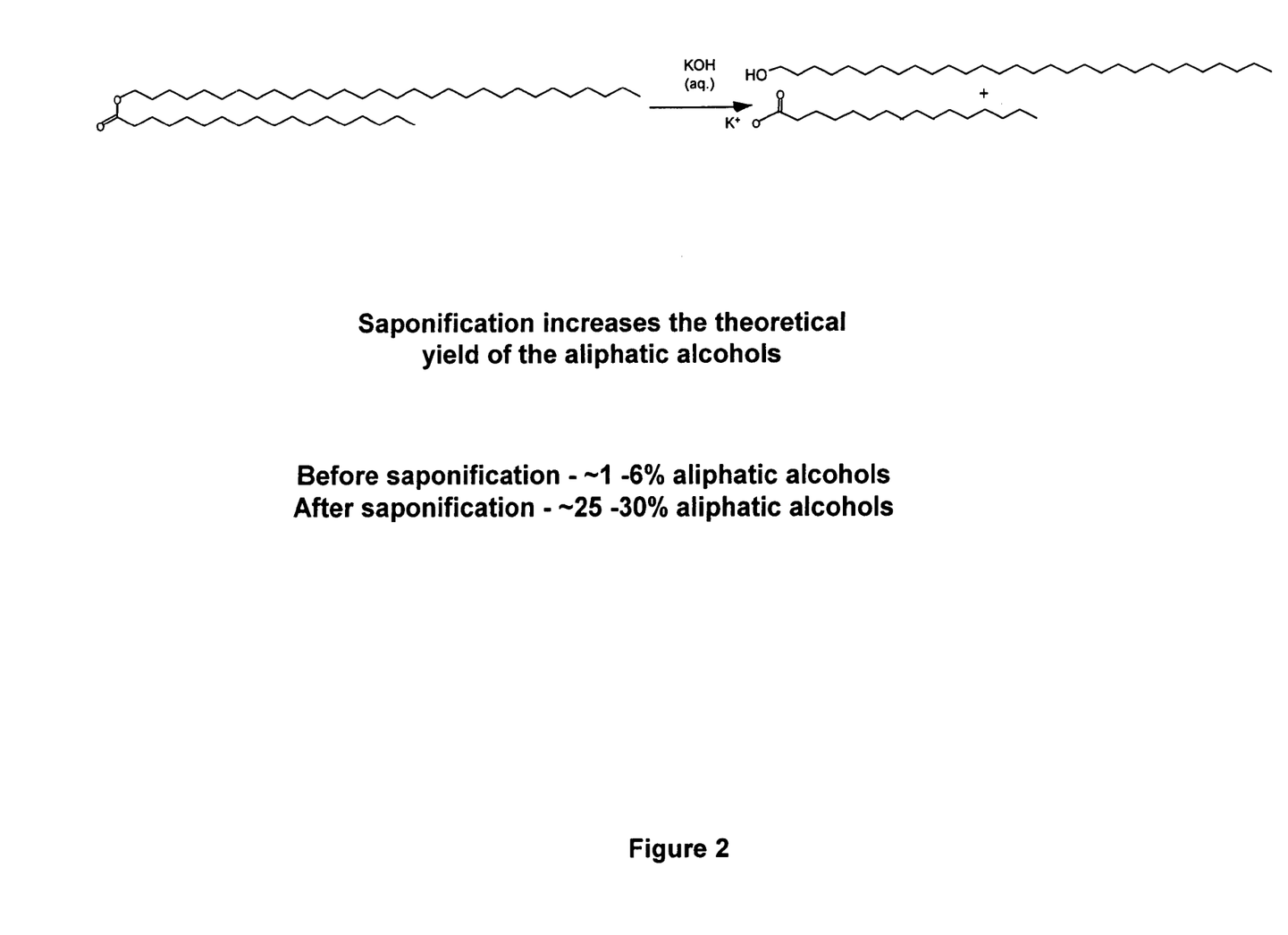
FIG. 2 is a reaction diagram depicting the theoretical yields as a result of the saponification step of the process according to the present invention.
Figure 3:
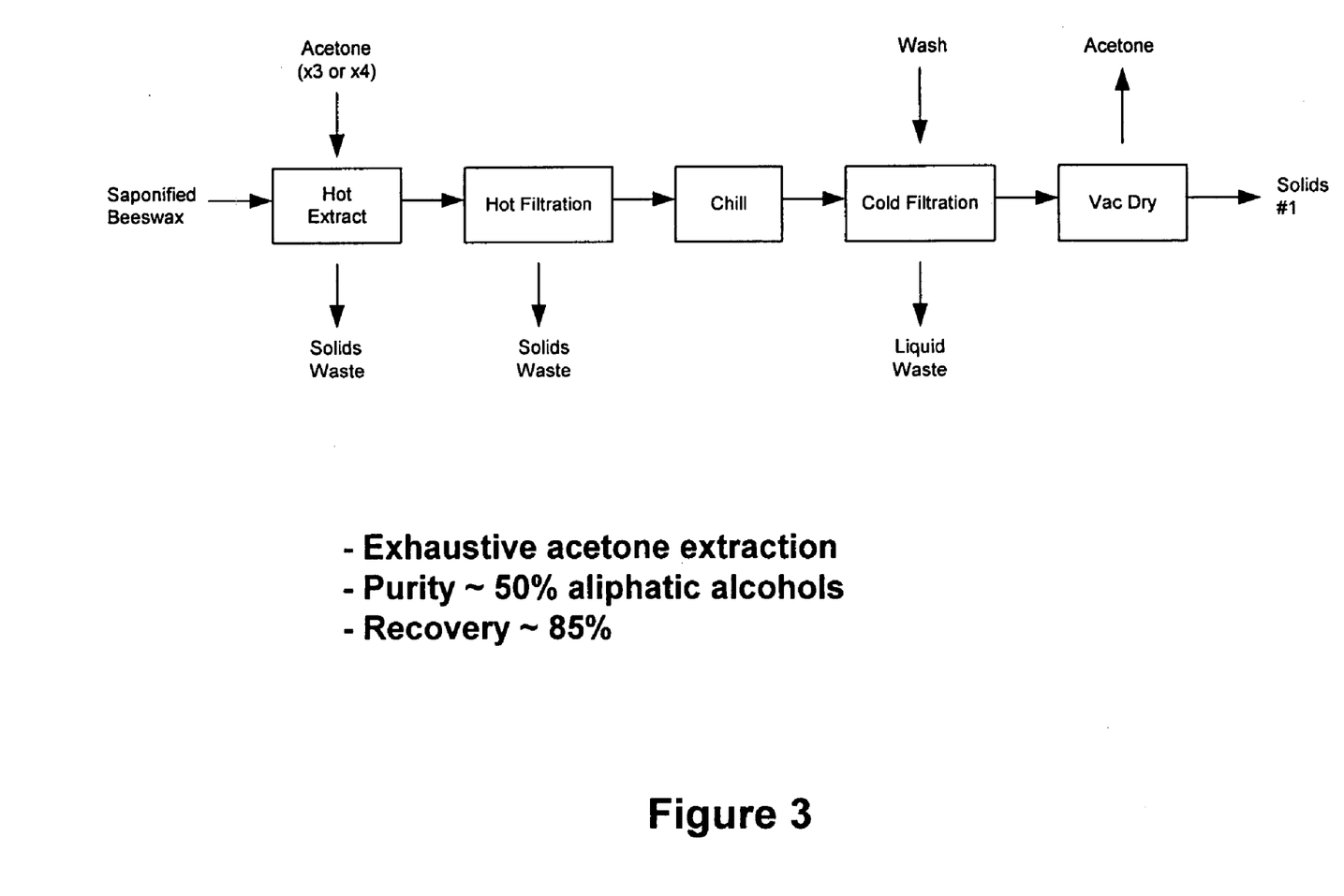
FIG. 3 is a flow diagram depicting the extraction step of the process according to the present invention.
Figure 4:
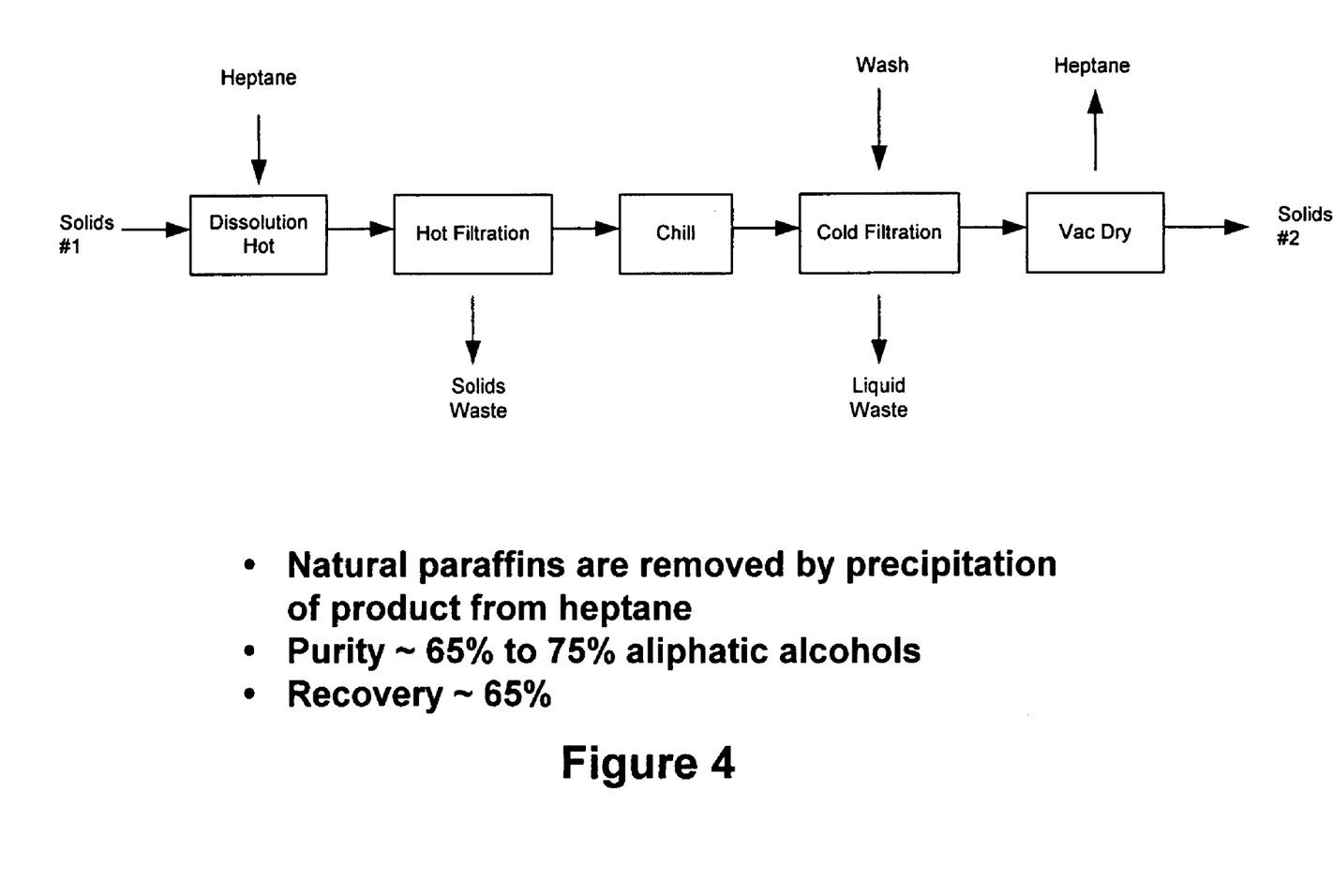
FIG. 4 is a flow diagram depicting the first purification step of the process according to the present invention.
Figure 5:
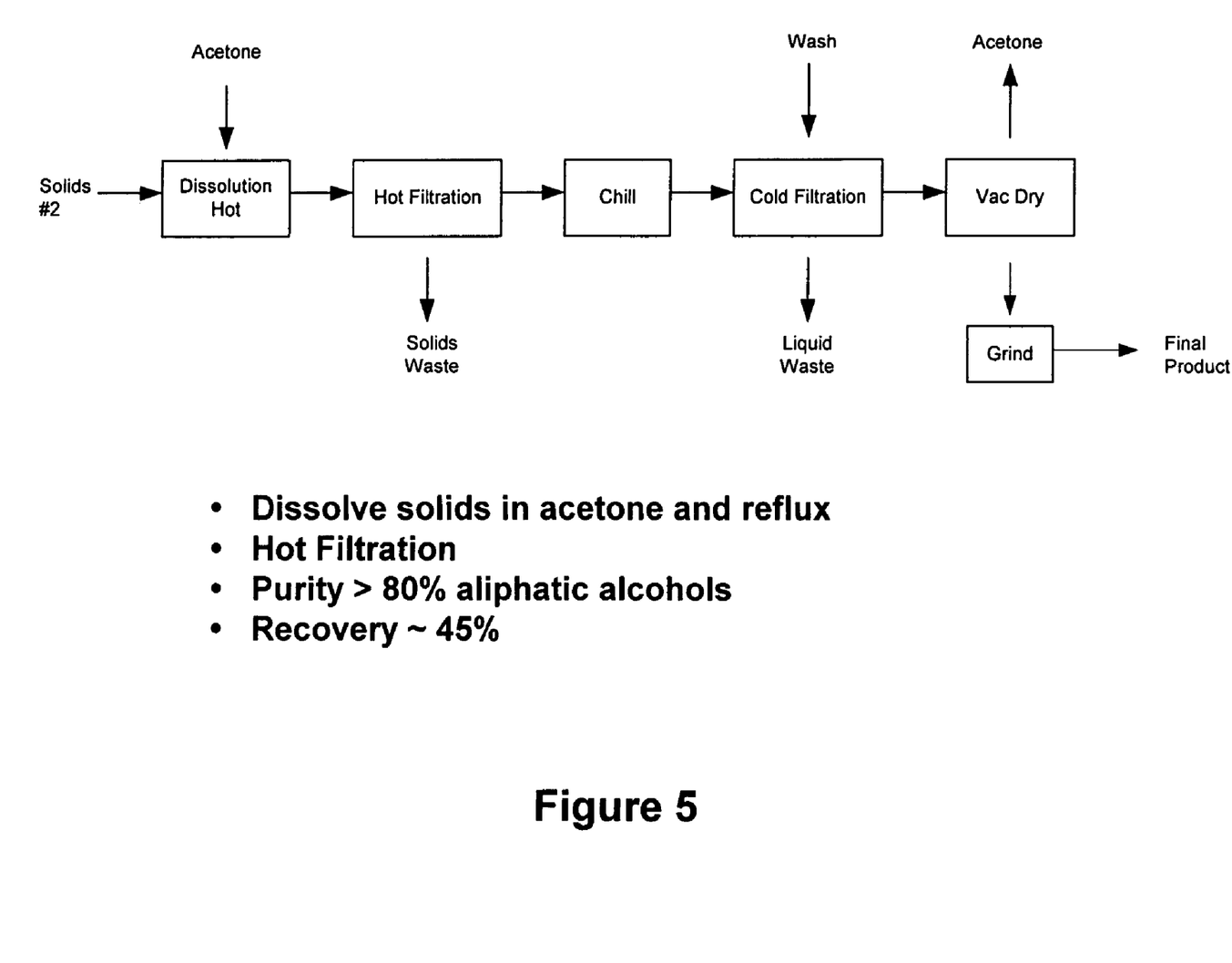
FIG. 5 is a flow diagram depicting the second purification step of the process according to the present invention.

The procedure for a homogeneous phase saponification process of beeswax in the present invention consists of melting the beeswax at a temperature of 80° C.–100° C., to which an aqueous solution of potassium hydroxide (10.7 M) is added with continuous stirring at 40–100 rpm. The saponification process is continued for 3 hours with continuous stirring at 80 rpm. It has been determined that each pound of wax requires between 38 grams and 47 grams of potassium hydroxide for complete saponification. The homogeneous phase saponification process of beeswax in the present invention increases the theoretical yield of the aliphatic alcohols as shown in FIG. 2. Yield is the only parameter affected when the beeswax is saponified or left unsaponified.

In a preferred embodiment, the cooled saponified beeswax is ground to achieve a particle size of 100–500 microns in diameter, preferably 250 microns in diameter. The particles of ground saponified beeswax are placed into a conventional solid-liquid extractor. A hot organic solvent extractant is also introduced into the extractor for contact with the particles of saponified beeswax contained therein. Preferably acetone is used as the extractant. However, other examples of suitable solvents, such as but not limited to, pentanone, toluene, benzene, ethanol, heptane, propanol, isopropanol, ethyl acetate, methanol, hexane, n-butanol, trichloroethane, methyl ethyl ketone, diethyl ether, 1,2-dichloroethane, dichloromethane, cyclohexane, chloroform and mixtures thereof may also be used. The ratio of beeswax particles to liquid extractant is from 1:4 to 1:8, preferably 1:6. Alternatively, rather than adding a hot organic solvent, water may be used as the extractant, and the extraction parameters are discussed in further detail below. The extraction is conducted for 3 to 7 hours, preferably 4 hours, within a temperature range of 50° C.–60° C., preferably 56° C. The beeswax particles are preferably agitated during the extraction procedure, for example by use of a rotating agitator to agitate the particles while in contact with the solvent. Advantageously the agitator is rotated at 40–100 rpm, preferably 80 rpm. During the extraction procedure the aliphatic alcohols become solubilized in the extractant thus leaving a waxy residue. Upon completion of the extraction, the extractant containing the aliphatic alcohols dissolved therein is removed from the waxy residue by filtration.

Next, the extract is introduced into a chamber for solidifying the aliphatic alcohols. These aliphatic alcohols are advantageously solidified by reducing the temperature of the extract in the chiller to form solids in the extractant (i.e., aliphatic alcohols in organic solvent solution). Preferably the temperature in the chiller should be uniform. An agitator may be provided within the vessel to assure a uniform temperature therein. The agitator is rotated at 40–80 rpm, preferably 60 rpm. The temperature during solidification is maintained within the range of 2° C.–10° C., preferably 6° C. for about 18 hours.

The suspension or mixture obtained from the chiller is vacuum-filtered or centrifuged to recover the solids. The solids are routinely washed with chilled solvent. Separation of the solids and liquids takes place by centrifuging the mixture or suspension at 1200–1400 rpm for about 2 hours. During centrifugation the particles may be washed with clean extraction solvent to remove contaminating material that may be present in the mother liquor.

The clean solid mixture (first solids) obtained from the centrifugation step is recovered and dried. Vacuum drying may be used. A pressure of 400 millibars at a temperature up to 50° C. may be used during the vacuum drying step.

The dried first solids obtained from the vacuum drying step are sent to a purifier where they are contacted with another hot organic solvent, which is preferably heptane in a heptane to solids ratio of 40:1. Other hot organic solvents such as, but not limited to, pentanone, toluene, ethanol, heptane, propanol, isopropanol, ethyl acetate, methanol, hexane, cyclohexane, n-butanol, trichloroethane, methyl ethyl ketone, 1,2-dichloroethane, dichloromethane, chloroform, diethyl ether, and mixtures thereof may also be used. The aliphatic alcohol solids are dissolved in the hot heptane to form a solution. The solution is hot-filtered before being introduced into a chiller for solidification. The same type of chiller may be used in the solidification step as was used in the initial solidification from the acetone. The temperature of the heptane solution is kept uniform by agitating with an agitator at 40–80 rpm, preferably 60 rpm. The temperature during resolidification is maintained at 15° C.–25° C., preferably 20° C. The resolidification step forms a mixture or suspension of solids in the heptane solvent.

The suspension or mixture of solids in the heptane is introduced into a filtration or centrifugation device where the solids are separated in the same manner as the solids were recovered from the acetone solvent. During this second filtration step, the solids can be washed with clean solvent (chilled heptane).

The particles (second solids) obtained from the second filtration step are then recovered and dried. Vacuum drying may be used. A pressure of 400 millibars at a temperature of up to 50° C. may be used during the vacuum drying step.

The dried solids obtained from the heptane purification step are sent to a purifier where they are contacted with another hot organic solvent which is preferably acetone at about 40 parts acetone to 1 part solids. Other organic solvents such as, but not limited to pentanone, toluene, ethanol, heptane, propanol, isopropanol, ethyl acetate, methanol, hexane, n-butanol, trichloroethane, methyl ethyl ketone, 1,2-dichloroethane, dichloromethane, chloroform, diethyl ether and mixtures thereof may also be used. The solids are dissolved in the acetone. The hot acetone solution is passed through a hot-filtration system. The filtered acetone solution is then introduced into a chiller for resolidification. The solidification is performed under similar conditions as the initial solidification of the alcohols from the acetone solution. Thus the same type of chiller may be used in this solidification step. The temperature of the hot acetone solution is kept uniform by agitating at 40–80 rpm, preferably 60 rpm. The temperature during resolidification is maintained at 2° C.–10° C., preferably 6° C. The resolidification step forms a mixture or suspension of solids in the acetone solvent.

The suspension or mixture of solids in the acetone is introduced into a filter, where it is filtered in the same manner that the solid suspension or mixture was filtered from the first acetone solvent. During this third filtration step, the crystals are washed with clean chilled solvent (acetone). The washed particles (third solids) obtained from the third filtration step are recovered and dried. Vacuum drying may be used. A pressure of 400 millibars at a temperature up to 35° C. may be used during the vacuum drying step.

After the particles are dried, they are then ready to be formulated into a conventional pharmaceutical formulation such as tablets, capsules, etc., for administration.

The yield (i.e., percent recovery by weight of alcohols with respect to the weight of aliphatic alcohols in saponified beeswax) obtained ranges about 40% with purity ranges typically from 80% to 99%. The natural mixture obtained contains aliphatic alcohols ranging from 20 to 34 carbon atoms, with a melting point between 61° C. and 65° C. The natural mixture of aliphatic alcohols obtained by this process may be analyzed through gas chromatography or HPLC.

In another embodiment, water is substituted for acetone in the first extraction step of the aliphatic alcohols purification (as described previously above).

Saponification is carried out as described previously. The cooled saponified beeswax or unsaponified beeswax is ground to achieve a particle size of 100–500 microns in diameter, preferably 250 microns in diameter. The particles of ground wax are placed into a conventional solid-liquid extractor. Water and an antifoaming agent, such as but not limited to Dow-Coming US1520 antifoam, are introduced into the mixture. The ratio of beeswax particles to water is from 1:6 to 1:12, preferably 1:10. The mixture is vigorously agitated for 3 to 7 hours, preferably 4 hours, at room temperature and then filtered using 10 µm filter cloth, such as but not limited to polyester or nylon, and a Buchner funnel. The beeswax particles are preferably agitated during the extraction procedure, for example by use of a rotating agitator to agitate the particles while in contact with the solvent. Advantageously the agitator is rotated at 40–100 rpm, preferably 80 rpm. During the extraction procedure the soaps (fatty acid salts) become solubilized in the extractant leaving the aliphatic alcohols as a solid. The recovered (first) solids are then dried.

The first solids thus obtained are then processed as discussed in detail above in the second step of the first embodiment by which the water extract solids are dissolved in a hot organic solvent, which is preferably heptane. Other hot organic solvents such as, but not limited to pentanone, toluene, ethanol, heptane, propanol, isopropanol, ethyl acetate, methanol, hexane, cyclohexane, n-butanol, trichloroethane, methyl ethyl ketone, 1,2-dichloroethane, dichloromethane, chloroform, diethyl ether, and mixtures thereof may also be used. The aliphatic alcohol solids are dissolved in the hot heptane to form a solution. Diatomaceous earth, such as but not limited to Celite 545, may be added to this hot solution. The heat is removed, and the solution is stirred vigorously until the temperature cools to room temperature. The temperature of the heptane solution is kept uniform by agitating with an agitator at 40–80 rpm, preferably 60 rpm. The resolidification step forms a mixture or suspension of solids in the heptane solvent. The solutions are filtered using Buchner funnels. The solids in the Buchner funnels are rinsed with fresh heptane at room temperature.

The heptane solids are then placed in a beaker with a stir bar and extracted with acetone at approximately 40° C.–65° C., preferably 55° C. for 2 hours. This extract is hot-filtered using a pre-warmed Buchner funnel. The extracts are chilled at approximately 5° C. overnight, and the solid precipitate is collected and dried.

This entire process gives good product purity. Using water as the first extraction solvent is effective, giving a 64% purity product with 58% aliphatic alcohol recovery.

In yet another embodiment, saponified beeswax is mixed with warm water. The ratio of saponified beeswax particles to warm water is 1:5 to 1:10 (preferably 1:5). The mixture is stirred. While stirring, ethanol is added at a ratio of 2 parts ethanol to 1 part homogenate followed by the addition of concentrated sulfuric acid until the pH is 2.5 to 1.0. The mixture is then cooled to approximately 50° C.–60° C., preferably 55° C., and the top (congealed) layer containing the aliphatic alcohols is removed and treated with cold water. Optionally these solids can be washed with ethanol. The solids are then recovered by filtration using a coarse filter and washed.

The procedures of this invention for obtaining the natural mixture of aliphatic alcohols from beeswax have some advantages compared to other prior art procedures.

Advantages of this invention (when using saponified beeswax) are related to the practical yields (10%–15% by weight) compared with the previously reported results with yields lower than 5%. Another advantage of the procedure relates to the purity that can typically be obtained (80%–99%) which is significantly higher than the purity in the prior art methods. Thus, the method of the present invention is simple and appropriate for large scale production.

The composition of the invention has new surprising pharmaceutical properties including anti-platelet, anti-inflammatory, anti-thrombotic and anti-schemic properties. In addition the composition is useful in the prevention of foam cell development, and the treatment of hypercholesterolemia. It also provides a protective effect on the vascular endothelium and can be used for the prevention of early atherosclerotic lesions (thrombus formation).

The pharmaceutical composition, foodstuffs, and dietary supplements formulated with the natural mixture of high purity aliphatic alcohols of this invention may be administered to humans and animals. The daily dosage of this natural mixture obtained from beeswax to be used for the reduction and/or prevention of hyper-cholesterolemic diseases, cholesterol, LDL-cholesterol, coronary heart disease (heart attacks and stroke), inflammation or immunoregulatory diseases, cardiovascular disease and neurodegenerative disorders is established between 1 to 100 mg per day (preferably 3 to 20 mg) and is intended for ingestion in any type or form of foodstuff, capsule, tablet or liquid form.

The present invention will become more clear from consideration of the following examples which are set forth to further illustrate the principles of the invention and are not intended, in any way, to be limiting thereof.

EXAMPLE 1

Organic Solvent Extraction

Saponification: Seven kg of beeswax were heated using a water bath at 80° C.–85° C. for 2.5 hours until the wax was completely melted. Once the wax was completely melted, 1.22 L of 10.7 M KOH in water were added dropwise over 30 minutes while continuing the stirring and heating. The mixture was held at temperature for 3 hours with stirring. After 3 hours the saponified wax was poured into trays and dried in a 60° C.–65° C. vacuum oven. The 7.5 kg of cooled dried saponified wax were then ground to a powder.

Extraction:

The saponified solids were placed in a 72 L round bottom flask along with 45 L of acetone. The acetone was brought to reflux and held there for 3 hours. The heat was then removed and the solids allowed to settle. The extract was decanted through cheesecloth into 5-gallon buckets. An additional forty-five liters of fresh acetone were added to the solids in the round bottom flask and the extraction and decantation repeated to generate a total of 3 filtered extracts. The extracts were chilled at 4° C.–8° C. for 40–45 hours, and the solids recovered by filtration using Buchner funnels and Whatman #4 filter paper. The 2.8 kg of collected solids were air dried for 48 hours.

Heptane Purification: The acetone extract solids (first solids) were dissolved in 60 L of heptane by holding the solution at 55° C.–65° C. for 2 hours with stirring. The hot solution was poured into five-gallon buckets which were sealed and cooled to 5° C. for 27 hours. The solutions were then filtered using Buchner funnels equipped with 50 μm monofilament nylon cloth. The solids in the Buchner funnels were rinsed with an additional 1.5 L of fresh heptane, and the solids dried in a vacuum oven at 45° C. and 15 inches of Hg to provide 1.9 kg of heptane solids.

Acetone Purification: The heptane solids (second solids) were extracted with 36 L of acetone at reflux for 2 hours. This extract was hot-filtered and put into sealed buckets. An equal volume of fresh acetone was added to the solids and the extraction repeated for an additional 2 hours. The extracts were chilled at approximately 5° C. for 42 hours, and the solid precipitate collected on Buchner funnels using Whatman #4 filter paper. The solids in the Buchner funnels were rinsed with an additional 1.5 L of fresh acetone and dried in a 35° C. vacuum oven for 17 hours to provide 0.94 kg of final product.

EXAMPLE 2

Single Center Study

The final product described above in Example 1 was used in an open label, single center study to evaluate the effectiveness and tolerability of aliphatic alcohols at lowering LDL-cholesterol, increasing HDL-cholesterol, lowering total cholesterol, and improving LDL-cholesterol/HDL-cholesterol ratio, the results of which are summarized below, involving 14 subjects who took 10 mgs of aliphatic alcohols per day for 6 weeks. There were no controls on the subjects' diets. All data are reported in mg/dL.

TABLE 1

| | TOTAL CHOLESTEROL | | | | |
|---|---|---|---|---|---|
| SUBJECT | T1 | T2 | % Chg | T3 | % Chg |
| 1 | 218 | 243 | 11% | 229 | 5% |
| 2 | 200 | 216 | 8% | 212 | 6% |
| 3 | 170 | 150 | −12% | 157 | −8% |
| 4 | 207 | 155 | −25% | 171 | −17% |
| 5 | 256 | 217 | −15% | 221 | −14% |
| 6 | 206 | 196 | −5% | 170 | −17% |
| 7 | 314 | 253 | −19% | 268 | −15% |
| 8 | 176 | 167 | −5% | 171 | 3% |
| 9 | 161 | 164 | 2% | 159 | −1% |
| 10 | 156 | 167 | 7% | 173 | 11% |

TABLE 1-continued

TOTAL CHOLESTEROL

| SUBJECT | T1 | T2 | % Chg | T3 | % Chg |
|---|---|---|---|---|---|
| 11 | 240 | N.T. | N/A | 220 | −8% |
| 12 | 212 | 185 | −13% | 184 | −13% |
| 13 | 260 | 212 | −18% | 224 | −14% |
| 14 | 231 | 208 | −10% | 241 | 4% |
| Average | 215 | 195 | −9% | 200 | −7% |
| p* | | | 0.06 | | 0.36 |

T1 = Baseline (before taking aliphatic alcohols)
T2 = 3 weeks of 10 mgs aliphatic alcohols per day
T3 = 6 weeks of 10 mgs aliphatic alcohols per day
N.T. = Not Tested,
N/A = Not Applicable
*Comparison with baseline by Wilcoxon statistical analysis

TABLE 2

TRIGLYCERIDES

| SUBJECT | T1 | T2 | % Chg | T3 | % Chg |
|---|---|---|---|---|---|
| 1 | 162 | 143 | −12% | 211 | 30% |
| 2 | 64 | 100 | 56% | 63 | −2% |
| 3 | 97 | 128 | 32% | 109 | 12% |
| 4 | 428 | 203 | −53% | 300 | −30% |
| 5 | 198 | 108 | −45% | 213 | 8% |
| 6 | 96 | 111 | 16% | 49 | −49% |
| 7 | 270 | 238 | −12% | 204 | −24% |
| 8 | 68 | 74 | 9% | 67 | −1% |
| 9 | 69 | 92 | 33% | 68 | −1 |
| 10 | 82 | 109 | 33% | 108 | 32% |
| 11 | 48 | N.T. | N/A | 99 | 106% |
| 12 | 213 | 220 | 3% | 196 | −8% |
| 13 | 125 | 186 | 49% | 185 | 48% |
| 14 | 155 | 119 | −23% | 118 | −24% |
| Average | 148 | 141 | −5% | 142 | 4% |
| p* | | | 1.00 | | 0.86 |

T1 = Baseline (before taking aliphatic alcohols)
T2 = 3 weeks of 10 mgs aliphatic alcohols per day
T3 = 6 weeks of 10 mgs aliphatic alcohols per day
N.T. = Not Tested,
N/A = Not Applicable
*Comparison with baseline by Wilcoxon statistical analysis

TABLE 3

HDL-Cholesterol

| SUBJECT | T1 | T2 | % Chg | T3 | % Chg |
|---|---|---|---|---|---|
| 1 | 41 | 42 | 2% | 40 | −2% |
| 2 | 48 | 45 | −6% | 60 | 25% |
| 3 | 32 | 31 | −3% | 33 | 3% |
| 4 | 38 | 41 | 8% | 49 | 29% |
| 5 | 59 | 69 | 17% | 63 | 7% |
| 6 | 50 | 51 | 2% | 58 | 16% |
| 7 | 61 | 54 | −11% | 66 | 8% |
| 8 | 49 | 45 | −8% | 54 | 10% |
| 9 | 54 | 49 | −9% | 48 | −11% |
| 10 | 60 | 56 | −7% | 71 | 18% |
| 11 | 63 | N.T. | N/A | 62 | −2% |
| 12 | 42 | 35 | −17% | 41 | −2% |
| 13 | 42 | 34 | −19% | 38 | −10% |
| 14 | 61 | 57 | −7% | 63 | 3% |
| Average | 50 | 47 | −6% | 53 | 5% |
| p* | | | 0.11 | | 0.008 |

T1 = Baseline (before taking aliphatic alcohols)
T2 = 3 weeks of 10 mgs aliphatic alcohols per day
T3 = 6 weeks of 10 mgs aliphatic alcohols per day
N.T. = Not Tested,
N/A = Not Applicable
*Comparison with baseline by Wilcoxon statistical analysis

TABLE 4

LDL-Cholesterol

| SUBJECT | T1 | T2 | % Chg | T3 | % Chg |
|---|---|---|---|---|---|
| 1 | 144.6 | 172.4 | 19% | 147.0 | 2% |
| 2 | 139.2 | 151.0 | 8% | 139.0 | 0% |
| 3 | 118.6 | 93.0 | −22% | 102.0 | −14% |
| 4 | N/A | 73.4 | N/A | 62.0 | N/A |
| 5 | 157.4 | 126.0 | −20% | 115 | −27% |
| 6 | 136.8 | 122.8 | −10% | 100 | −27% |
| 7 | 199.0 | 151.4 | −24% | 161.0 | 19% |
| 8 | 113.4 | 107.2 | −5% | 104.0 | −8% |
| 9 | 93.2 | 96.6 | 4% | 97 | 4% |
| 10 | 79.6 | 89.2 | 12% | 80.0 | 1% |
| 11 | 167.4 | N.T. | N/A | 138.0 | −18% |
| 12 | 127.4 | 106.0 | −17% | 104.0 | −18% |
| 13 | 183.0 | 140.8 | −23% | 149.0 | −19% |
| 14 | 139.0 | 127.2 | −8% | 154.0 | 11% |
| Average | 138.0 | 120.0 | −13% | 118.0 | −15% |
| p* | | | 0.11 | | 0.03 |

T1 = Baseline (before taking aliphatic alcohols)
T2 = 3 weeks of 10 mgs aliphatic alcohols per day
T3 = 6 weeks of 10 mgs aliphatic alcohols per day
N.T. = Not Tested,
N/A = Not Applicable
*Comparison with baseline by Wilcoxon statistical analysis

TABLE 5

Cardiovascular Disease Risk (CDR)

| SUBJECT | T1 | T2 | % Chg | T3 | % Chg |
|---|---|---|---|---|---|
| 1 | 5.32 | 5.79 | 9% | 5.73 | 8% |
| 2 | 4.17 | 4.80 | 15% | 3.53 | −15% |
| 3 | 5.31 | 4.84 | −9% | 4.76 | −10% |
| 4 | 5.45 | 3.78 | −31% | 3.49 | −36% |
| 5 | 4.34 | 3.14 | −28% | 3.51 | −19% |
| 6 | 4.12 | 3.84 | −7% | 2.93 | −29% |
| 7 | 5.15 | 4.69 | −9% | 4.06 | −21% |
| 8 | 3.59 | 3.71 | 3% | 3.17 | −12% |
| 9 | 2.98 | 3.35 | 12% | 3.31 | 11% |
| 10 | 2.60 | 2.98 | 15% | 2.44 | −6% |
| 11 | 3.81 | N.T. | N/A | 3.55 | −7% |
| 12 | 5.05 | 5.29 | 5% | 4.49 | −11% |
| 13 | 5.92 | 6.24 | 5% | 5.89 | −1% |
| 14 | 3.79 | 3.65 | −4% | 3.83 | 1% |
| Average | 4.40 | 4.32 | −2% | 3.91 | −11% |
| p* | | | 0.26 | | 0.01 |

T1 = Baseline (before taking aliphatic alcohols)
T2 = 3 weeks of 10 mgs aliphatic alcohols per day
T3 = 6 weeks of 10 mgs aliphatic alcohols per day
N.T. = Not Tested,
N/A = Not Applicable
*Comparison with baseline by Wilcoxon statistical analysis As demonstrated by the data in the above tables, there was a 15% reduction in LDL-cholesterol that is statistically significant at 97% confidence level.

The 7% reduction in total cholesterol is not statistically significant. While the 3 week data had shown a 9% reduction and was statistically significant at 94% confidence level, the 6 week data do not support this trend. The most likely explanation is that of diet, which was not controlled in this study.

It is important to note that with an uncontrolled diet it is not uncommon to see an increase in total cholesterol and LDL-cholesterol over the course of the study. This has been demonstrated in the placebo group in other aliphatic alcohols studies, see M. Canetti, et al., "A two-year study on the efficacy and tolerability of aliphatic alcohols in patients with type II hyperlipoproteinemia," *Int J Clin Pharm Res*, 15(4): 159–165 (1995).

A 7% increase in HDL-cholesterol levels, 92% confidence level, was observed and was not unexpected. Prior studies in humans have shown an increase in HDL levels.

The CDR was reduced by 11%, 99% confidence level. This is due to the decreased total cholesterol and increased HDL-cholesterol levels and was expected.

There was no improvement in triglycerides, and this was expected. Most prior studies using aliphatic alcohols have indicated no significant reduction in triglycerides.

The data looked promising. Previous studies of aliphatic alcohols, from sugar cane by P. Pons, et al., "Effects of successive dose increases of aliphatic alcohols on the lipid profile of patients with type II hypercholesterolaemia and tolerability to treatment," *Int. J. Clin. Pharm. Res.*, 14(1): 27–33 (1994), demonstrated an 8% reduction in total cholesterol in 8 weeks with 5 mg/day and a 14% reduction in total cholesterol in 16 weeks with 5 mg/day for the first 8 weeks and then 10 mg/day for the remaining 8 weeks. They also reported an 11% and 22% reduction in LDL-cholesterol from the same study. These data are consistent with the results of the current study and one would expect to see further reduction in both LDL-cholesterol and total cholesterol if the study duration were increased.

EXAMPLE 3

Water Extraction

The use of water extraction as an alternative to the first acetone extraction step of the aliphatic alcohol purification (as disclosed in Example 1 above) was evaluated below. Initial experiments had shown that extracting with water as a first step could provide a product of similar purity to that obtained by the typical first acetone extraction. This approach was pursued by tracking solids and aliphatic alcohol recoveries through the process and taking the first product through the heptane and acetone purification steps to demonstrate the ability of this approach to make a suitable product. The experiment and results are described below.

Saponification: Saponification was carried out as described previously.

First Extraction: Approximately, 100.3 g of saponified beeswax (31% purity; 31 g aliphatic alcohols) were placed in a 2 L round bottom flask along with 1 L water and 3 drops of Dow-Corning US1520 antifoam. The mixture was shaken vigorously for 3 minutes and then filtered using 10 μm monofilament nylon filter cloth and a Buchner funnel. An additional liter of fresh water was used to further wash the solids. The first solids that remain were dried, giving 28 g at 64% purity with 58% aliphatic alcohols recovery.

Heptane Purification: The water extract solids (first solids) from above were dissolved in 500 mL of heptane by holding the solution at 70° C. in an oil bath for 1 hour with stirring. To this hot solution, 14 g of Celite 545 were added and the suspension stirred at temperature for one additional hour. The heat was removed, and the solution was stirred overnight at room temperature. The solution was then filtered using a Buchner funnel equipped with VWR 417 paper. The second solids in the Buchner funnel were rinsed with an additional 300 mL of fresh heptane at room temperature.

Acetone Purification: The heptane solids (second solids) were placed in a beaker with a stir bar and extracted with 500 mL of acetone at approximately 55° C. for 2 hours. This extract was hot-filtered using a pre-warmed Buchner funnel and 10 μm polyester cloth and placed into a sealed beaker. A heat gun was used to keep the solution from cooling during the filtration. The extracts were chilled at approximately 5° C. overnight and then the solid precipitate collected on a Buchner funnel using Whatman #4 filter paper. The final product solids obtained were assayed at 97% purity.

Conclusion: This entire process gave good product purity. Using water as the first extraction solvent was an effective step.

EXAMPLE 4

Alternate Water/Extraction

About 20.0 g of saponified beeswax containing approximately 5.1 g of aliphatic alcohols were mixed with 100 mL of warm water (60° C.) until the mixture formed an emulsion. While stirring 185 mL of 95% ethanol was added and the mixture was warmed to 60° C.–70° C. Next 1.6 mL of concentrated sulfuric acid were added. Stirring and heating were continued until the solution boiled and all the solids disappeared. The mixture was set aside to cool with a temperature probe. When the mixture reached 55° C., the top layer of congealed aliphatic alcohols were removed and placed in a beaker of cold water. The aliphatic alcohols was collected on a coarse filter, washed with water and room temperature ethanol. Approximately 8.7 g of aliphatic alcohols were recovered with an aliphatic alcohol purity of about 46% and recovery of about 78%.

EXAMPLE 5

Alternate Solvents for Aliphatic Alcohols Extraction and Purification from Beeswax Alternate solvents for the aliphatic alcohols extraction from beeswax were investigated on the bench. The isolation and purification method followed was basically the process described previously. Microgranulated saponified beeswax was used as the starting material. Eight different solvent systems were used to extract and purify the aliphatic alcohols and were compared with the current solvent system. The solvent systems tested were as follows: acetone/heptane/acetone; heptane/acetone/ethyl acetate; ethyl acetate/heptane/ethyl acetate; methyl ethyl ketone/hexane/methyl ethyl ketone; isopropyl alcohol/heptane/isopropyl alcohol; isopropyl alcohol/cyclohexane/isopropyl alcohol; diethyl ether/hexane/diethyl ether; ethanol/heptane/ethanol; and methanol/hexane/methanol. All extractions were carried out by soxhlet extraction except for the diethyl ether extraction. Due to its low boiling point and extreme flammability, the diethyl ether extraction was carried out at room temperature. The total aliphatic alcohols content in the intermediate and final products were determined, and the purities of the products were compared (see Table 6). The entire program is outlined below using the first solvent system (acetone/heptane/acetone) as an example.

Experimental:

Extraction with Solvent 1 (i.e., Acetone): About 35 g of saponified beeswax was added to a tared extraction thimble (33×118 mm). A soxhlet was set up with a 500 mL round-bottom flask. About 245 mL of Solvent 1 were added to the flask and connected to the soxhlet system. The system was refluxed for approximately 4–5 hours, and the extract was quickly decanted into a 400 mL beaker. The extract was chilled at approximately 0° C.–4° C. overnight. The chilled extract was then filtered through a Whatman #1 filter paper, and the collected solids were washed with approximately 245 mL of Solvent 1 at room temperature. The solids were air dried (Sample A).

Extraction with Solvent 2 (i.e., Heptane): About 12 g of Sample A were weighed into a tared extraction thimble (25×100 mm). Then 240 mL of Solvent 2 were added to a 500 mL round-bottom flask, and the flask connected to the soxhlet system. The liquid was brought to reflux. The solution was refluxed for approximately 4–5 hours. The heat was removed, and the solution quickly decanted into a 400 mL beaker. The extract was chilled at approximately 0° C.–4° C. overnight. The chilled extract was filtered through a Whatman #1 filter paper, and the solids washed by pouring approximately 84 mL of room-temperature Solvent 2 through the filtration system. The solids were air dried (Sample B).

Extraction with Solvent 3 (i.e., Acetone): About 5 g of Sample B were weighed into a tared extraction thimble (25×110 mm). Then 245 mL of Solvent 3 were added to a 250 mL round-bottom flask, and the flask connected to the soxhlet system. The system was refluxed for approximately 4–5 hours, removed from the heat, and the extract quickly decanted into a 400 mL beaker. The extract was chilled at approximately 0° C.–4° C. overnight. The chilled extract was filtered through a Whatman #1 filter paper, and the solids washed by pouring approximately 245 mL of room-temperature Solvent 3 through the filtration system. The solids were air dried (Sample C).

Aliphatic alcohol analysis: Intermediate and final products were analyzed for total aliphatic alcohol content and aliphatic alcohol recovery.

Results: Table 6 shows a comparison of aliphatic alcohols content in the extracts.

TABLE 6

Purity and Recovery of Aliphatic Alcohols Using Different Solvent Systems

| Solvent System No | | % Purity of Aliphatic Alcohols | % Recovery of Aliphatic Alcohols | Change in Purity × Recovery |
|---|---|---|---|---|
| | Starting Material | 22–32 | N/A | |
| 1 | Acetone | 43–55 | 41–54 | 10.5 |
| | Heptane | 69–84 | 95–100 | 26.8 |
| | Acetone | 92–96 | 92–100 | 20.6 |
| | Overall | | | 30.7 |
| 2 | Heptane | 33.1 | 79.9 | 4.9 |
| | Acetone | 87.1 | 103 | 55.6 |
| | EtOAc | 88.2 | 95.2 | 1.0 |
| | Overall | | | 47.9 |
| 3 | MEK | 38.6 | 84.4 | 9.8 |
| | Hexane | 62.7 | 97.9 | 23.6 |
| | MEK | 77.6 | 97.7 | 14.6 |
| | Overall | | | 40.8 |
| 4 | IPA | 33.5 | 82.8 | 6.8 |
| | Heptane | 46.1 | 89.6 | 11.3 |
| | IPA | 50.5 | 96.2 | 4.2 |
| | Overall | | | 16.8 |
| 5 | EtOAc | 56.3 | 92.5 | 27.1 |
| | Heptane | 86.0 | 93.6 | 27.8 |
| | EtOAc | 87.2 | 82.3 | 1.0 |
| | Overall | | | 42.9 |
| 6 | IPA | 34.0 | 97.5 | 6.8 |
| | Cyclohexane | 72.5 | 60.5 | 23.3 |
| | IPA | 72.5 | 91.3 | 0 |
| | Overall | | | 24.5 |
| 7 | $Et_2O$ | 33.2 | 88.7 | 5.5 |
| | Hexane | 92.0 | 40.4 | 23.8 |
| | $Et_2O$ | N/D | N/D | |
| | Overall | | | 23.3 |
| 8 | EtOH | 40.2 | 102 | 13.5 |
| | Heptane | 45.4 | 79.5 | 4.1 |
| | EtOH | 53.7 | 88.6 | 7.4 |
| | Overall | | | 19.2 |
| 9 | MeOH | 32.8 | 27.2 | 1.6 |
| | Hexane | 50.1 | 97.5 | 16.9 |
| | MeOH | 46.7 | 40.9 | 0 |
| | Overall | | | 2.1 |

Discussion:

Starting material (saponified beeswax) was analyzed by GC and showed 27.9% aliphatic alcohol content. This material was processed by soxhlet extraction as described above. The aliphatic alcohol purity varied greatly depending on the extraction solvent. All product component ratios were similar to the starting material except for the methanol solvent system.

In the first solvent extraction, ethyl acetate gave the highest purity (56%) and all other solvents gave extracts over 33% pure. Ethanol extraction gave the best recovery (~100%) with 40% purity. Acetone as first extraction solvent (in the current process) showed poor recovery (41~54%) and was one of the worst recoveries of the tested solvent systems, but the purity was second best. The first soxhlet extraction using either heptane or ethyl acetate was difficult because of plugging problems in the extraction apparatus. Diethyl ether extraction was carried out at room temperature with stirring. The filtration of the diethyl ether solution was also very difficult since the extract formed an emulsion. The difficulty of filtration of the first extraction can be ranked as follows (most difficult to least): diethyl ether > methanol > ethanol > heptane > isopropanol > ethyl acetate > acetone > methyl ethyl ketone. The success of all first solvent processes based on change in purity times recovery can be ranked as: ethyl acetate > ethanol > methyl ethyl ketone > isopropanol > diethyl ether > heptane > acetone > methanol (as listed in Table 6).

In the second solvent extraction, the aliphatic alcohol purity was increased to as high as 92% by using hexane to extract the diethyl ether first extract. Heptane/acetone and ethyl acetate/heptane solvent systems were able to achieve greater than 86% purity. Acetone/heptane, isopropanol/cyclohexane and methyl ethyl ketone/hexane were between 77% and 63% purity. The other solvent systems, such as methanol/hexane, isopropanol/heptane and ethanol/heptane, were all below 50% purity. The aliphatic alcohols recovery was above 90% for the second extraction of the following solvent systems: heptane/acetone, methyl ethyl ketone/acetone, acetone/heptane and methanol/hexane. Even though the purity from the diethyl ether/hexane extraction was the highest at 92%, its recovery of 40% was not acceptable. Since more impurities had been removed, the extraction and filtration processes of all the second solvent materials went more smoothly than the first step. Heptane and hexane as second extraction solvents showed much less difficulty in the extraction and filtration than they did as first extraction solvents.

In the third solvent extraction, the aliphatic alcohol purity was over 90% by the acetone/heptane/acetone solvent system, and over 80% by the heptane/acetone/ethyl acetate and ethyl acetate/heptane/ethyl acetate solvent systems. The third extraction of the methanol/hexane/methanol solvent system showed only about 40% recovery. All final extractions, filtrations and dryings were easy to control except methanol and ethanol. Solubility in methanol was high enough that there was a great deal of loss during filtration, and this extract was also difficult to dry. Only about 40% of the aliphatic alcohols solid were recovered in the last methanol extraction.

Of the nine solvent systems, heptane/acetone/ethyl acetate, methyl ethyl ketone/hexane/methyl ethyl ketone and ethyl acetate/heptane/ethyl acetate gave better results than the current solvent system (acetone/heptane/acetone). It should be mentioned there were some problems during the processing with these three solvent systems. There was difficulty in the extraction using either heptane or ethyl acetate as a first extraction solvent. The soxhlet frequently plugged and was not easily melted. The filtration of the heptane extract was even harder than it was when heptane was used as the second solvent extraction (current production process). The filtration of the ethyl acetate extract was faster than the heptane extract. Even though the methyl ethyl ketone/hexane/methyl ethyl ketone solvent system did not achieve 80% purity goal (it was 78%), it showed the best behavior through all the process steps. The extraction, filtration and drying steps all went easily.

The final products with the best overall appearance were from using methyl ethyl ketone and ethyl acetate as the third solvent. This could be applied to the current process, so that the final grinding step could be limited.

EXAMPLE 6

Alternate Natural Sources of Aliphatic Alcohols

A. Alternate Wax Sample Preparation: For wax samples (such as Candellia wax or Carnauba wax) each was accurately weighed (20 g) into an 80 mL beaker and placed into a 95° C. oil bath. Slowly 3.5 mL of 10.7 M KOH were added to the melted wax. The sample was saponified for 3 hours with stirring and air dried for over 18 hours at room temperature. The dried saponified wax was ground into small pieces using a coffee grinder. An 18 g sample was accurately weighed and transferred to a 25×100 mm extraction thimble, and then soxhlet extracted with 126 mL of acetone for 5 hours.

B. Alternate Oil Sample Preparation: For oil samples (such as peanut oil, sesame oil, Norwegian cod liver oil, oat oil, and rice bran oil), each was accurately weighed (20 g) into an 80 mL beaker and placed into a 95° C. oil bath. Slowly 3.5 mL of 10.7 M KOH was added with stirring. The sample was held at temperature for 3 hours. The oily saponified material was air dried overnight and chilled at 0° C. for about 5 hours. Twenty grams of the sample were quickly weighed into a 25×100 mm extraction thimble and soxhlet extracted with 200 mL of acetone for 5 hours.

C. Alternate Powder Sample Preparation: For powder samples (such as rice bran or bee pollen), twenty-two grams of each was accurately weighed into a 100 mL beaker and placed into a 95° C. oil bath. Slowly 3.9 mL of 10.7 M KOH and 45 mL of DI water were added with stirring. The samples were heated for 3 hours and air dried for about 18 hours. The saponified wax was ground into small pieces using a coffee grinder. A 20 g sample was transferred into a 25×100 mm extraction thimble and soxhlet extracted with 250 mL of acetone for 5 hours.

D. Alternate Needle Sample Preparation: Thirty grams of rosemary needles were weighed into a 48×123-mm extraction thimble. Heptane (300 mL) was added to a 500 mL round-bottom flask and extracted for 5 hours in a soxhlet extraction system. The heptane extract was evaporated by rotary evaporator at 50° C. to dryness. The solids were heated in a 95° C. oil bath and 15 mL of DI water were added to make a slurry. Saponification was carried out by slowly adding 0.4 mL of 10.7 M KOH and holding at temperature for 3 hours. The saponified solids obtained were freeze-dried for about 18 hours and ground into small pieces using a coffee grinder. A 2 g sample was transferred into a 25×100 mm extraction thimble, and soxhlet extracted with 100 mL of acetone for 5 hours.

Figure 6:
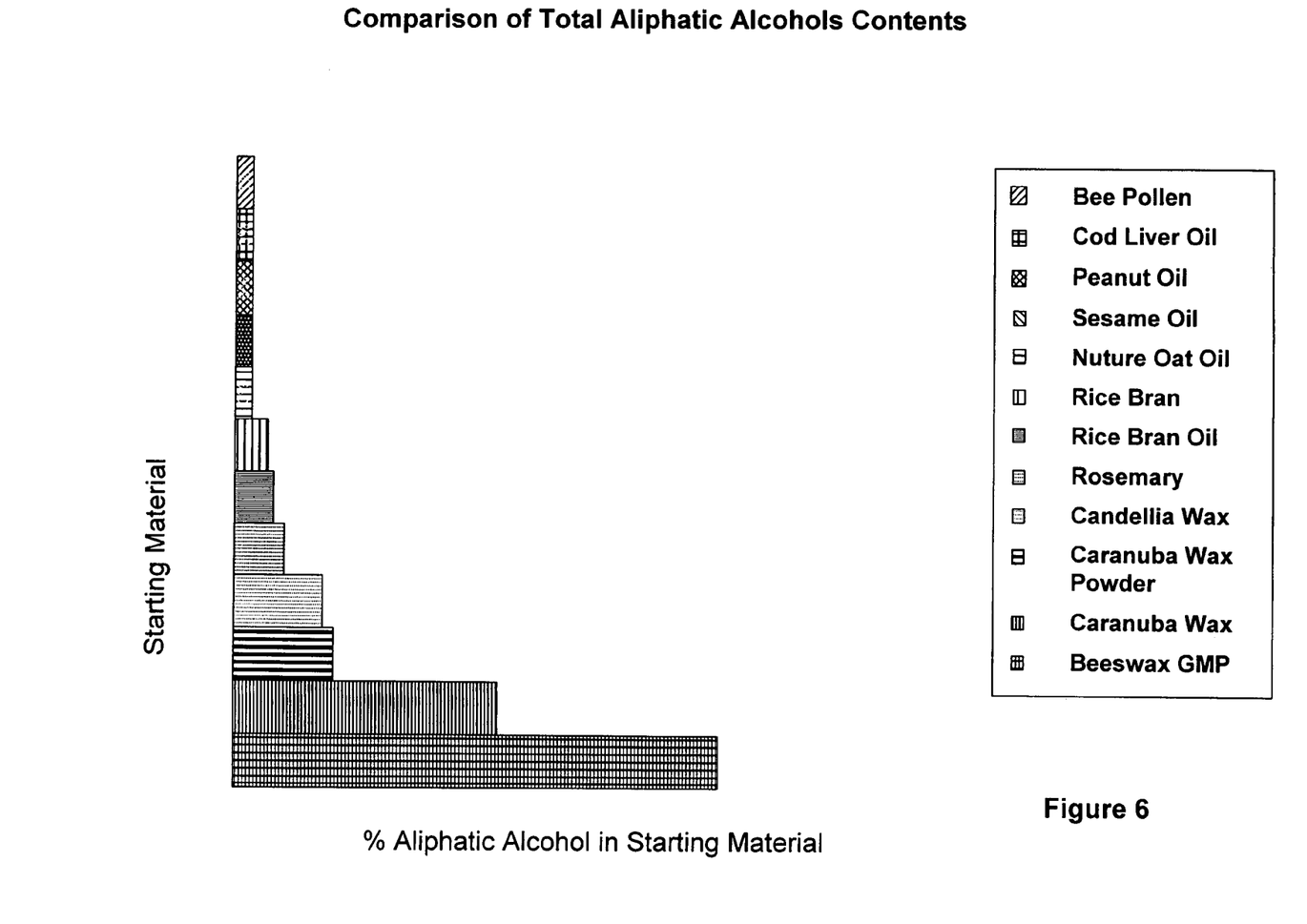
FIG. 6 shows the range of total aliphatic alcohols content for alternative natural materials.

All final acetone extracts were separately evaporated to dryness without exceeding 50° C. The percentage of aliphatic alcohols in the starting material was calculated based on the total aliphatic alcohol content in each acetone extract. The range of aliphatic alcohol contents for all above processed materials is shown in FIG. 6. Gas chromatography analysis for individual aliphatic alcohol percentages are listed in Table 7. The data for aliphatic alcohols from beeswax is from the current GMP process. The most aliphatic alcohols were found in beeswax, which was as high as 30% aliphatic alcohol. Carnauba wax contained about 17%, candellia wax about 5%, rosemary about 3% and rice bran oil 2% aliphatic alcohol.

temperature for an additional hour. The solution was mixed and cooled to room temperature and filtered using a Buchner funnel.

The solids (54.01 g) were dried and ground using a coffee grinder. A column was prepared (5 cm diameter, 100 g of Mallinkrodt Silicar 6512) and the ground solids were added to it. The column was eluted with: heptane, 25% acetone/heptane, acetone, and methanol. All fractions were chilled overnight in a 5° C. refrigerator and then filtered using a Buchner funnel and VWR 417 paper. The solids obtained were air dried and assayed.

TABLE 7

Alternate Sources of Aliphatic Alcohols

| Source Starting Material | Aliphatic alcohols % in Acetone Extract | Aliphatic alcohols % in Starting Material | Percentage of Each Aliphatic Alcohol | | | | | | | | |
|---|---|---|---|---|---|---|---|---|---|---|---|
| | | | C-20 | C-22 | C-24 | C-26 | C-27 | C-28 | C-30 | C-32 | C-34 |
| Bee Pollen | 2.5 | 0.12 | 8 | 19 | 13 | 11 | 3 | 0 | 27 | 8 | 0 |
| Rice Bran Powder | 0.8 | 0.17 | 3 | 2 | 3 | 2 | 2 | 11 | 68 | 8 | 0 |
| Rosemary | 47.9 | 2.6 | 0 | 0 | 0 | 7 | 2 | 68 | 16 | 8 | 0 |
| Carnauba Wax | 49.2 | 16.9 | 0 | 0 | 3 | 0 | 0 | 5 | 16 | 77 | 0 |
| Candella Wax | 8.5 | 5.3 | 0 | 0 | 0 | 5 | 13 | 16 | 42 | 24 | 0 |
| Nuture Oat Oil | 1.0 | 0.95 | 36 | 0 | 0 | 0 | 0 | 0 | 54 | 0 | 0 |
| Rice Bran Oil | 2.0 | 1.86 | 5 | 14 | 8 | 5 | 7 | 14 | 27 | 18 | 0 |
| Peanut Oil | 0.2 | 0.06 | 0 | 0 | 0 | 0 | 0 | 0 | 100 | 0 | 0 |
| Sesame Oil | 0.3 | 0.15 | 0 | 0 | 0 | 0 | 0 | 0 | 100 | 0 | 0 |
| Carnauba Wax Powder | 21.1 | 5.6 | 0 | 0 | 0 | 0 | 0 | 50 | 21 | 74 | 0 |
| Cod Liver Oil | 0.2 | 0.14 | 0 | 0 | 0 | 0 | 0 | 100 | 0 | 0 | 0 |
| Saponified Beeswax (Current Process) | 51.0 | 30.6 | 0 | 0 | 18 | 17 | 0 | 19 | 31 | 15 | 0 |

EXAMPLE 7

Purification of Aliphatic Alcohol Using Chromatography

The feasibility of using a silica column to purify the aliphatic alcohols in saponified beeswax was investigated. Experiments in the past had failed since applying the heptane solids directly to the column caused it to plug nearly immediately. However, it has been discovered that coating the material onto Celite and then putting that combination onto the column minimized the plugging.

Experiment A:

Extraction: Approximately 131 g of saponified beeswax was placed into a 1 gallon bottle along with 1 L water and 3 drops of Dow-Corning US1520 antifoam. The mixture was shaken vigorously for 3 minutes and then filtered using a 10 µm monofilament nylon cloth and a Buchner funnel. An additional liter of fresh water was added to the solids in the Buchner funnel to further wash the solids. The collected solids were air dried (39.8 g of about 30% purity) for 48 hours.

Column Purification: The water-insoluble solids were dissolved in 200 mL of heptane by holding the solution at 70° C. in an oil bath for 1 hour with stirring. To this hot solution 20 g of Celite 545 were added and stirred at

TABLE 8

| Volume (L) | Elution Solvent | Purity (%) | Solids (g) | Aliphatic Alcohols (g) |
|---|---|---|---|---|
| | Starting Material | 31 | 131 | 40.7 |
| 0.5 | 100% heptane | N/A | 0 | 0 |
| 1 | 25% acetone heptane | 96 | 2.44 | 2.34 |
| 1 | 25% acetone heptane | 93 | 2.87 | 2.67 |
| 1 | 100% acetone | 83 | 0.49 | 0.40 |
| 1 | 100% acetone | N/A | 0 | 0 |
| 1 | 100% methanol | 4 | 0.61 | 0.02 |

CONCLUSIONS

This provided a good purity product. The aliphatic alcohol recovery was 46%. Further work could improve the recovery from this process.

A second column was run by thoroughly mixing the saponified beeswax into silica, then loading onto a silica column and eluting with vacuum. This worked well and demonstrated less plugging.

Experiment B:

Using a 2.5 cm diameter column with a sintered glass frit at bottom. About 18.6 g of saponified wax (22% aliphatic alcohols) was placed into a 1 L round bottom flask with 34.5 g of silica gel and 200 mL of 1:1 tetrahydrofuran/heptane. This slurry was rotovapped to dryness and then the solids were ground in a coffee grinder to a powder. This material was placed onto a column. A vacuum pump was used to pull the solvents through the column with the following results. Eluted in the manner described in Table 9.

TABLE 9

| Volume (L) | Elution Solvent | Purity (%) | Solids (g) | Aliphatic Alcohols (g) |
|---|---|---|---|---|
| 0.3 | 100% heptane | 20 | 2.086 | 0.44 |
| 0.1 | 100% heptane | 100 | 0.162 | 0.16 |
| 0.15 | 50% heptane/acetone | 65 | 0.901 | 0.60 |
| 0.15 | 50% heptane/acetone | 66 | 0.461 | 0.30 |
| 0.25 | 50% heptane/acetone | 66 | 0.480 | 0.32 |
| 0.6 | 50% heptane/acetone | 65 | 1.272 | 0.83 |
| 0.15 | 100% acetone | 56 | 0.121 | 0.07 |

Results:

Pooling the second through last fraction would provide 56% aliphatic alcohols recovery at approximately 65% purity. The column plugged during the acetone elution, so further recovery was not possible.

EXAMPLE 7

Dissolution of Dosage Units

Maltodextrin (75.1 g), calcium stearate (2.3 g), and aliphatic alcohols (95% purity; 4.52 g) were thoroughly mixed together and the resulting powder used to fill #0 hard gelatin capsules. The average capsule fill weight was 192 mg and each capsule contained 10 mg of aliphatic alcohols. The dissolution of these capsules was measured using USP paddles (Apparatus 2) at 100 rpm in 500 mL of 0.5% (w/v) sodium lauryl sulfate (SLS) about 37° C. Samples were removed from the dissolution vessel using a cannula fitted with a 30 micron filter after 60 and 120 minutes.

The dissolution samples were analyzed by HPLC with ELSD detection. The HPLC analysis utilized a 4.6×150 mm Luna (2) C-8 column running 100% methanol at 1.5 mL/minute. A standard curve was generated by injecting pure aliphatic alcohol standard in dissolution medium equivalent to 20, 10, 5, 4 and 2 µg/mL.

Only trace amounts of aliphatic alcohols were observed in chromatograms of the samples. The total amount of aliphatic alcohols dissolved corresponded to 0.5–0.7 mg or 5–7% of the amount in the dosage units.

A second dry blend capsule formulation was prepared which substituted microcrystalline cellulose for maltodextrin. The dissolution for these capsules used the conditions described above and was also poor (less than 10%).

In a third variation, the aliphatic alcohols were micronized by placing 10 g in a 125 mL plastic bottle with 5 stainless steel balls (0.8 cm diameter.) and placing the bottle on a shaker for 24 hours. The micronized aliphatic alcohols were formulated with maltodextrin and magnesium stearate such that each capsule contained the equivalent of 10 mg of aliphatic alcohols, 259 mg of maltodextrin, and 11 mg of magnesium stearate. The dissolution for these capsules using the conditions described above was no better than that observed for the unmicronized aliphatic alcohols (<10%).

EXAMPLE 8

Dissolution of Dosage Units

A simulated wet-granulation formulation was prepared as follows: 27.5 mg of aliphatic alcohol (85% purity) were placed in a small vial with 4 mL of acetone; the acetone was warmed to boiling to dissolve the aliphatic alcohol and 759 mg of maltodextrin were added and mixed with the acetone solution in order to coat the maltodextrin with a thin film of aliphatic alcohols. After the paste was cooled to room temperature, the acetone was removed under vacuum. The dissolution of aliphatic alcohols in 400 mg of this sample was determined by stirring it with 500 mL of dissolution medium at 37° C. for 1 hour. HPLC analysis with ELSD detection indicated that 7.6 mg of the 11.9 mg of aliphatic alcohols contained in the sample dissolved after 1 hour (64%).

EXAMPLE 9

Dissolution of Dosage Units

A simulated soft-gelatin capsule formulation was prepared as follows: 31.6 mg of (85% purity), 996 mg of canola oil and 74 mg of soy lecithin were mixed together while warming to about 60° C., whereupon the aliphatic alcohols dissolved in the vegetable oil. After removing some undissolved lecithin the mixture was cooled to room temperature where it congealed to form a uniform suspension. Approximately 912 mg of the mixture containing 10 mg of aliphatic alcohols were subjected to a simulated dissolution test using a stir bar and 500 mL of dissolution medium at about 37° C. The data indicated that roughly 100% of the aliphatic alcohols dissolved in this formulation.

A second experiment utilized a formulation composed of aliphatic alcohols (61.2 mg of 85% purity), canola oil (1713 mg) and lecithin (108 mg) and was prepared similarly to the previous experiment. A portion (541 mg) of the gel containing 15 mg of aliphatic alcohols was put into a #0 hard gelatin capsule and tested for aliphatic alcohols dissolution using the conditions described in Example 1. HPLC analysis with ELSD detection indicated that 10 mg of the 15 mg contained in the dosage unit dissolved after 1 hour (67%).

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The embodiments of the invention in which an exclusive property or privilege is claimed are defined as follows:

1. A method of manufacturing a mixture of primary alcohols comprising the steps of:
   obtaining a starting material containing a mixture of aliphatic alcohols and non-alcoholic compounds,
   grinding said starting said material containing primary aliphatic alcohols into particles;

subjecting the particles to liquid extraction with a liquid organic extractant in which said alcohols are soluble; and recovering said alcohol mixture from said extractant, whereby said alcohol mixture is isolated from said non-alcoholic compounds contained in said starting material and the resulting mixture comprises

| 1-eicosanol | C-20 | 0–5% |
|---|---|---|
| 1-docosanol | C-22 | 0–5% |
| 1-tetracosanol | C-24 | 12–30% |
| 1-hexacosanol | C-26 | 13–30% |
| 1-heptacosanol | C-27 | 0–5% |
| 1-octacosanol | C-28 | 12–25% |
| 1-triacontanol | C-30 | 20–40% |
| 1-dotriacontanol | C-32 | 5–15% |
| 1-tetratriacontanol | C-34 | 0–5%. |

2. The method of claim 1 wherein said liquid organic extractant is selected from the group comprising: acetone, toluene, benzene, ethanol, heptane, hexane, pentanone, methanol, propanol, isopropanol, ethyl acetate, diethyl ether, trichioroethane, methyl ethyl ketone, n-butanol, 1,2-dichloroethane, dichioromethane, chloroform and mixtures thereof; and said isolated alcohol mixture has a purity level of 80–99% with respect to said non-alcoholic compounds contained in said starting material.

3. The method of claim 1 wherein said starting material is selected from the group consisting of waxes, beeswax, carnauba wax, candellia wax, bee pollen, oil, peanut oil, sesame oil, cod liver oil, rice bran oil, oat oil, rosemary needle oil, powders, and rice bran.

4. The method of claim 1, wherein said isolated alcohol mixture has a purity level of 80–99% aliphatic alcohols with respect to said non-alcoholic compounds contained in said starting material.

5. The method of claim 1 wherein said mixture of said aliphatic alcohols are micronized.

* * * * *